United States Patent
Kiazand et al.

(10) Patent No.: US 11,847,415 B2
(45) Date of Patent: Dec. 19, 2023

(54) AUTOMATED DETECTION OF SAFETY SIGNALS FOR PHARMACOVIGILANCE

(71) Applicant: Astrazeneca AB, Sodertalje (SE)

(72) Inventors: Alexandre Kiazand, Gaithersburg, MD (US); Robert Hernandez, Cambridge (GB); Antoni Wisniewski, Peterborough (GB); Douglas Domalik, Wilmington, DE (US); Tony Gill, Nottingham (GB)

(73) Assignee: AstraZeneca AB, Sodertalje (SE)

( * ) Notice: Subject to any disclaimer, the term of this patent is extended or adjusted under 35 U.S.C. 154(b) by 375 days.

(21) Appl. No.: 17/382,946

(22) Filed: Jul. 22, 2021

(65) Prior Publication Data
US 2022/0100958 A1    Mar. 31, 2022

Related U.S. Application Data

(60) Provisional application No. 63/085,762, filed on Sep. 30, 2020.

(51) Int. Cl.
*G06F 40/279* (2020.01)
*G16H 70/40* (2018.01)
(Continued)

(52) U.S. Cl.
CPC .......... *G06F 40/279* (2020.01); *G06F 40/30* (2020.01); *G06N 20/00* (2019.01); *G16H 70/40* (2018.01)

(58) Field of Classification Search
CPC ...... G06F 40/216; G06F 40/279; G06F 40/30; G06N 3/08; G06N 20/00; G16H 70/40
See application file for complete search history.

(56) References Cited

U.S. PATENT DOCUMENTS

| 9,075,796 | B2 | 7/2015 | Markatou et al. |
| 9,836,455 | B2 * | 12/2017 | Martens ............... G06F 40/279 |

(Continued)

OTHER PUBLICATIONS

Alammar, The Illustrated Transformer—Visualizing machines learning one concept at a time, Aug. 12, 2020, 23 pages.
(Continued)

*Primary Examiner* — Mohammad K Islam
(74) *Attorney, Agent, or Firm* — McDonnell Boehnen Hulbert & Berghoff LLP

(57) ABSTRACT

An embodiment may involve obtaining a set of pre-defined features and a new document; extracting a subset of the pre-defined features from within new document; applying a natural language model to the new document, wherein the natural language model was pre-trained using scientific or medical literature and fine-tuned using a corpus of documents; applying a feature-based model to the subset of the pre-defined features extracted from the new document, wherein the feature-based model was trained with the pre-defined features and the respective labels of the documents; and applying an aggregation model to the classifications of the new document produced by the natural language model and the feature-based model, wherein the aggregation model was trained with prior classifications produced by the natural language model and the feature-based model so that the aggregation model produces a further classification of the new document representing its relevance to pharmacovigilance.

20 Claims, 12 Drawing Sheets

(51) Int. Cl.
*G06N 20/00* (2019.01)
*G06F 40/30* (2020.01)

(56) References Cited

U.S. PATENT DOCUMENTS

| | | | |
|---|---|---|---|
| 10,614,196 B2 | 4/2020 | Maitra et al. | |
| 11,182,545 B1* | 11/2021 | Tsai | G06N 20/10 |
| 11,657,222 B1* | 5/2023 | Anthony | G06F 40/279 |
| | | | 706/12 |
| 2016/0092793 A1 | 3/2016 | Garrow et al. | |
| 2017/0372233 A1 | 12/2017 | Dolan | |
| 2018/0308569 A1 | 10/2018 | Luellen | |
| 2018/0365248 A1* | 12/2018 | Zheng | G06F 40/216 |
| 2019/0272725 A1 | 9/2019 | Viklund et al. | |
| 2020/0042580 A1* | 2/2020 | Davis | G06F 16/93 |
| 2020/0111023 A1* | 4/2020 | Pondicherry Murugappan | G06N 5/02 |
| 2020/0311205 A1* | 10/2020 | Büttner | G06F 40/216 |
| 2021/0201018 A1* | 7/2021 | Patel | G06Q 30/0201 |
| 2021/0209142 A1* | 7/2021 | Tagra | G06N 3/044 |
| 2023/0004604 A1* | 1/2023 | Li | G06F 18/22 |
| 2023/0139831 A1* | 5/2023 | Wang | G06V 30/1444 |
| | | | 704/9 |

OTHER PUBLICATIONS

Devlin et al., BERT: Pre-training of Deep Bidirectional Transformers for Language Understanding, May 19, 2019, 16 pages.
Hansson et al., Semantic text mining in early drug discovery for type 2 diabetes, PLOS ONE, Jun. 15, 2020, 18 pages.
Jon Stevens et al., Representing document-level semantics of biomedical literature using pre-trained embedding models, Proceedings of the 15th Conference on Natural Language Processing (KONVENS 2019), 5 pages.
Jinhyuk Lee et al., BioBERT: a pre-trained biomedical language representation model for biomedical text mining, Bioinformatics, 2019, pp. 1-7.
Iz Beltagy et al., SCIBERT: A Pretrained Language Model for Scientific Text, Sep. 10, 2019, 6 pages.
Semantic Analytics: An integrated approach for pharmacovigilance teams to achieve total awareness, SciBite, 5 pages.

* cited by examiner

| TYPE | NAME | ID | REFERENCE | SENTENCE(S) |
|---|---|---|---|---|
| DRUG | SAXGLIPTIN | CHEMBL385517 | https://www.ebi.ac.uk/chembl/compound/inspect/CHEMBL385517 | 23,24 |
| GENE | DIPEPTIDYL PEPTIDASE 4 | DPP4 | http://www.genenames.org/cgi-bin/gene_symbol_report?match=DPP4 | 23 |
| MEDICAL CONDITION | HYPOGLYCAEMIA | MDR10020993 | | 24 |
| MEDICAL CONDITION | TYPE 2 DIABETES | MDR10067585 | | 23 |

FIG. 6A drug/ae: Drug indexed with /AE in Embase
drug_abstract: Drug name/synonym found in the abstract
drug_title: Drug name/synonym found in the title
drug_keywords: Drug name/synonym found in the keywords
stats_abstract: Statistical term found in the abstract
risk_odds_abstract: Risk score or odds ratio term found in the abstract
kur_abstract: KUR term found in the abstract
kur_title: KUR term found in the title
kur_keywords: KUR term found in the keywords
dme_abstract: DME term found in the abstract
dme_title: DME term found in the title
dme_keywords: DME term found in the keywords
listed_abstract: Listed term found in the abstract
listed_title: Listed term found in the title
listed_keywords: Listed term found in the keywords
mdrae_abstract: MedDRA term found in the abstract
mdrae_title: MedDRA term found in the title
mdrae_keywords: MedDRA term found in the keywords
special_pop_abstract: Special population found in the abstract
sentence_drug_mdrae: Drug name/synonym and MedDRA term found in the same sentence
sentence_drug_kur: Drug name/synonym and KUR term found in the same sentence
sentence_drug_dme: Drug name/synonym and DME term found in the same sentence
sentence_drug_listed: Drug name/synonym and listed term found in the same sentence
sentence_drug_special_pop: Drug name/synonym and special population found in the same sentence
sentence_stats_mdrae: Statistical term and MedDRA term found in the same sentence
sentence_stats_kur: Statistical term and KUR term found in the same sentence
sentence_stats_dme: Statistical term and DME term found in the same sentence
sentence_stats_listed: Statistical term and listed term found in the same sentence
sentence_risk_odds_mdrae: Risk score or odds ratio term and MedDRA term found in the same sentence
sentence_risk_odds_kur: Risk score or odds ratio term and KUR term found in the same sentence
sentence_risk_odds_dme: Risk score or odds ratio term and DME term found in the same sentence
sentence_risk_odds_listed: Risk score or odds ratio term and listed term found in the same sentence
sentence_sae_mdrae: 'Serious' or 'SAE' and MedDRA term found in the same sentence
sentence_sae_kur: 'Serious' or 'SAE' and KUR term found in the same sentence
sentence_sae_dme: 'Serious' or 'SAE' and DME term found in the same sentence
sentence_sae_listed: 'Serious' or 'SAE' and listed term found in the same sentence
sentence_ae_mdrae: Adverse event or adverse reaction MedDRA entity and any other MedDRA term found in the same sentence
sentence_ae_kur: Adverse event or adverse reaction MedDRA entity and KUR term found in the same sentence
sentence_ae_dme: Adverse event or adverse reaction MedDRA entity and DME term found in the same sentence
sentence_ae_listed: Adverse event or adverse reaction MedDRA entity and listed term found in the same sentence
sentence_product_issues: 'Product packaging' synonyms and 'problem' synonyms found in the same sentence
is_case_report: 'Case report' mentioned in the abstract or keywords
contains_fatal_abstract: 'Fatal' synonyms found in the abstract
citescore: Journal impact factor from Scopus
time_in_review: Difference between the article review date and earliest recorded review date for the drug in question (to approximate the age of a drug at the time of review)
num_az: Number of times AstraZeneca is mentioned in the abstract (to identify AZ-sponsored studies)
is_azd: Whether the drug has an AZD code name
is_medi: Whether the drug has a MEDI code name

FIG. 6B

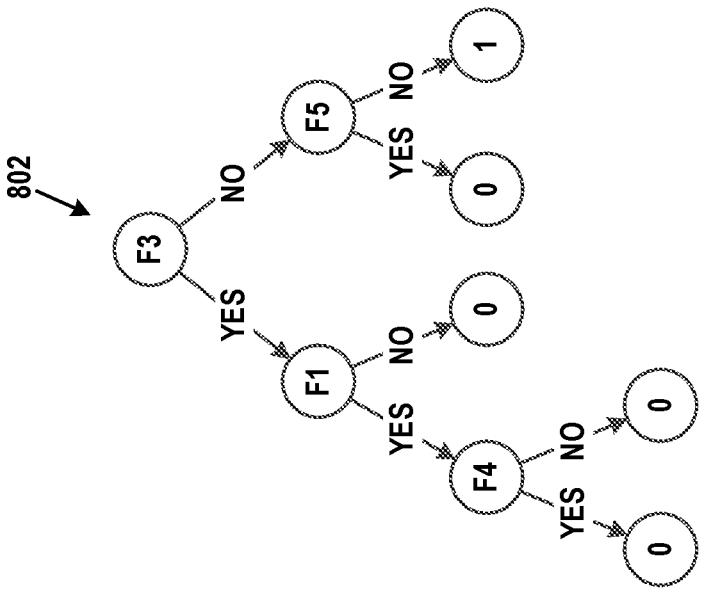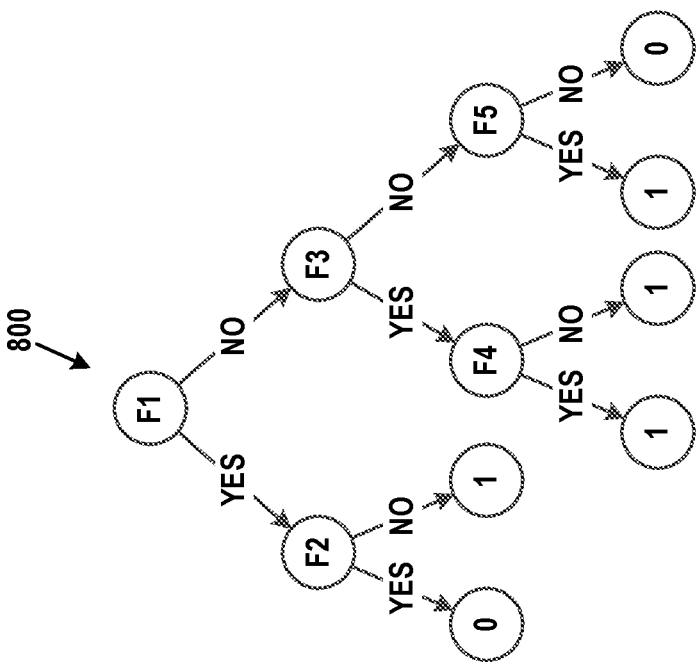
FIG. 8

AUTOMATED DETECTION OF SAFETY SIGNALS FOR PHARMACOVIGILANCE

CROSS-REFERENCE TO RELATED APPLICATION

This application claims priority to U.S. provisional patent application No. 63/085,762, filed Sep. 30, 2020, which is hereby incorporated by reference in its entirety.

BACKGROUND

A difficult problem in the development and ongoing management of pharmaceuticals is pharmacovigilance, an aspect of which is the detection of safety signals that may impact the risk/benefit profile of a drug. In particular, pharmacovigilance attempts to determine whether there is evidence of a relationship between administration of a drug and an adverse event. If this is the case, then it may be further determined whether there is an underlying causation, i.e., to what extent the adverse event may have been caused by the administration. For example, if 10% of all patients to whom a particular drug is administered have a specific adverse event (e.g., a dangerous drop in blood pressure), then a number of actions could be taken, from continuous monitoring of the drug, to changing the labeling of the drug, to removing the drug from the market.

But these causations are notoriously difficult to accurately identify, due to the complex nature of human physiology and because many patients are simultaneously taking a number of drugs. Thus, it is crucial to be able to monitor as many data points and data sources as possible—ideally the totality of data within all available data sources—to evaluate possible correlations. Sources for this data includes scientific and medical literature, adverse event reports, filings with regulatory agencies, and so on.

The sheer volume of this data is overwhelming, including hundreds of thousands of papers, reports, and other documents from various public and private databases. Often, highly-trained medical professionals, such as doctors, are required to review this data, document by document, seeking safety signals. Importantly, safety signals often need to be identified very quickly. For instance, if a significant safety signal is published, it is beneficial to the health and safety of patients for this signal to be identified within a few days or less so that the appropriate actions can be taken. In particular, these time constraints make it virtually impossible for all relevant safety signals to be identified by way of human review. Moreover, manual review generates a large number of false positives and false negatives, as medical professionals with different backgrounds or levels of expertise may identify safety signal in different ways.

SUMMARY

The embodiments herein address these and other problems by providing a hybrid suite of automated natural language processing algorithms that can be used to identify safety signals in documents. With these techniques, the documents can be classified into two categories—of interest or not of interest. Documents classified as being of interest may contain terms, phrases, and/or patterns of language that are indicative of a safety signal, while documents with no identified safety signals are classified as being not of interest. The vast majority of articles (e.g., about 97% in practice) will fall into the latter category.

With the number of articles flagged for manual review dramatically decreased, the medical professionals can focus more on evaluating the strengths of the identified safety signals, to what extent these signals are indicative of adverse events caused by drugs, and the actions (if any) that should be taken.

Accordingly, a first example embodiment may involve obtaining, from persistent storage, a corpus of documents, wherein each of the documents is labelled with its relevance to pharmacovigilance. The first example embodiment may further involve performing data preparation operations on the documents, wherein the data preparation operations include: de-duplicating the documents, normalizing terminology within the documents, and extracting pre-defined features within the documents, wherein the pre-defined features relate to pharmacovigilance. The first example embodiment may further involve fine-tuning a natural language model with the documents and their labels, wherein the natural language model was pre-trained using scientific or medical literature, and wherein the fine-tuning involves further training of one or more encoders within the natural language model so that the natural language model seeks to classify new documents in accordance with their relevance to pharmacovigilance. The first example embodiment may further involve training a feature-based model with the pre-defined features extracted from the documents and the respective labels of the documents so that the feature-based model also seeks to classify the new documents in accordance with their relevance to pharmacovigilance, wherein the feature-based model utilizes a plurality of decision trees with nodes representing the pre-defined features. The first example embodiment may further involve training an aggregation model with classifications produced by the natural language model and the feature-based model so that the aggregation model seeks to produce further classifications of the new documents in accordance with their relevance to pharmacovigilance, wherein the further classifications are weighted combinations of classifications produced by the natural language model and the feature-based model for the new documents.

A second example embodiment may involve obtaining, from persistent storage, a set of pre-defined features and a new document related to a scientific or medical topic, wherein the pre-defined features relate to pharmacovigilance. The second example embodiment may further involve normalizing terminology within the new document. The second example embodiment may further involve extracting a subset of the pre-defined features from within new document. The second example embodiment may further involve applying a natural language model to the new document, wherein the natural language model was pre-trained using scientific or medical literature and fine-tuned using a corpus of documents, wherein each of the documents was labelled with its relevance to pharmacovigilance, and wherein the fine-tuning involved further training of one or more encoders within the natural language model so that the natural language model seeks to classify the new document in accordance with its relevance to pharmacovigilance. The second example embodiment may further involve applying a feature-based model to the subset of the pre-defined features extracted from the new document, wherein the feature-based model was trained with the pre-defined features and the respective labels of the documents so that the feature-based model also seeks to classify the new document in accordance with its relevance to pharmacovigilance, wherein the feature-based model utilizes a plurality of decision trees with nodes representing the pre-defined features. The second example embodiment may further involve applying an aggregation model to the classifications of the new document produced by the natural language model and the feature-based model, wherein the aggregation model was trained with prior classifications produced by the natural language model and the feature-based model so that the aggregation model seeks to produce a further classification of the new document in accordance with its relevance to pharmacovigilance, wherein the further classification is a weighted combination of classifications produced by the natural language model and the feature-based model for the new document.

In a third example embodiment, an article of manufacture may include a non-transitory computer-readable medium, having stored thereon program instructions that, upon execution by a computing system, cause the computing system to perform operations in accordance with the first and/or second example embodiment.

In a fourth example embodiment, a computing system may include at least one processor, as well as memory and program instructions. The program instructions may be stored in the memory, and upon execution by the at least one processor, cause the computing system to perform operations in accordance with the first and/or second example embodiment.

In a fifth example embodiment, a system may include various means for carrying out each of the operations of the first and/or second example embodiment.

These, as well as other embodiments, aspects, advantages, and alternatives, will become apparent to those of ordinary skill in the art by reading the following detailed description, with reference where appropriate to the accompanying drawings. Further, this summary and other descriptions and figures provided herein are intended to illustrate embodiments by way of example only and, as such, that numerous variations are possible. For instance, structural elements and process steps can be rearranged, combined, distributed, eliminated, or otherwise changed, while remaining within the scope of the embodiments as claimed.

BRIEF DESCRIPTION OF THE DRAWINGS

FIG. 6A depicts results of feature extraction from a corpus of documents, in accordance with example embodiments.

FIG. 6B depicts a list of features with possible relevance to classification of documents, in accordance with example embodiments.

FIG. 8 depicts a tree-based gradient-boosting model, in accordance with example embodiments.

DETAILED DESCRIPTION

Example methods, devices, and systems are described herein. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features unless stated as such. Thus, other embodiments can be utilized and other changes can be made without departing from the scope of the subject matter presented herein.

Accordingly, the example embodiments described herein are not meant to be limiting. It will be readily understood that the aspects of the present disclosure, as generally described herein, and illustrated in the figures, can be arranged, substituted, combined, separated, and designed in a wide variety of different configurations. For example, the separation of features into "client" and "server" components may occur in a number of ways.

Further, unless context suggests otherwise, the features illustrated in each of the figures may be used in combination with one another. Thus, the figures should be generally viewed as component aspects of one or more overall embodiments, with the understanding that not all illustrated features are necessary for each embodiment.

Additionally, any enumeration of elements, blocks, or steps in this specification or the claims is for purposes of clarity. Thus, such enumeration should not be interpreted to require or imply that these elements, blocks, or steps adhere to a particular arrangement or are carried out in a particular order.

I. EXAMPLE COMPUTING DEVICES AND CLOUD-BASED COMPUTING ENVIRONMENTS

The embodiments herein may involve the use of various types of computing systems and environments. The following embodiments describe architectural and functional aspects of example computing systems, as well as the features and advantages thereof.

Figure 1:
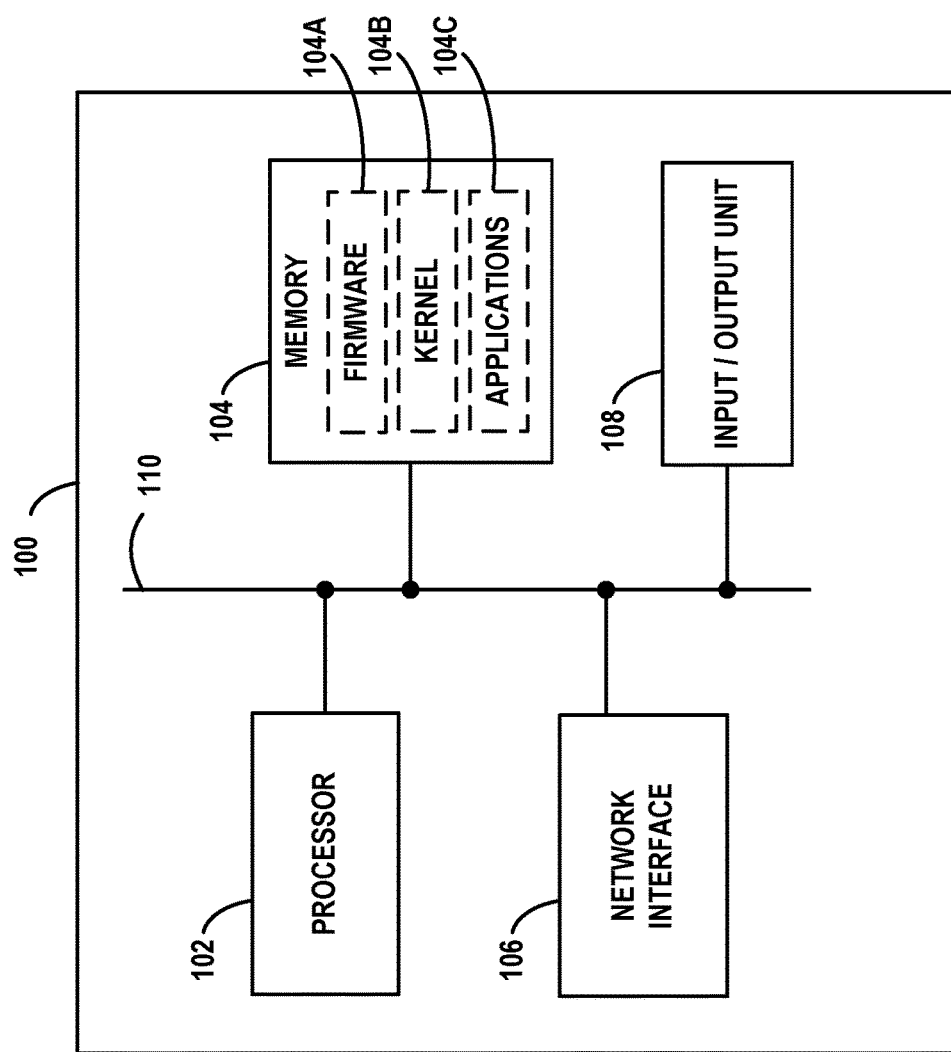
FIG. 1 illustrates a schematic drawing of a computing device, in accordance with example embodiments.

FIG. 1 is a simplified block diagram exemplifying a computing device 100, illustrating some of the components that could be included in a computing device arranged to operate in accordance with the embodiments herein. Computing device 100 could be a client device (e.g., a device actively operated by a user), a server device (e.g., a device that provides computational services to client devices), or some other type of computational platform. Some server devices may operate as client devices from time to time in order to perform particular operations, and some client devices may incorporate server features.

In this example, computing device 100 includes processor 102, memory 104, network interface 106, and an input/output unit 108, all of which may be coupled by a system bus 110 or a similar mechanism. In some embodiments, computing device 100 may include other components and/or peripheral devices (e.g., detachable storage, printers, and so on).

Processor 102 may be one or more of any type of computer processing element, such as a central processing unit (CPU), a co-processor (e.g., a mathematics, graphics, encryption, or tensor co-processor), a digital signal processor (DSP), a network processor, and/or a form of integrated circuit or controller that performs processor operations. In some cases, processor 102 may be one or more single-core processors. In other cases, processor 102 may be one or more multi-core processors with multiple independent processing units. Processor 102 may also include register memory for temporarily storing instructions being executed and related data, as well as cache memory for temporarily storing recently-used instructions and data.

Memory 104 may be any form of computer-usable memory, including but not limited to random access memory (RAM), read-only memory (ROM), and non-volatile memory (e.g., flash memory, hard disk drives, solid-state drives, compact discs (CDs), digital video discs (DVDs), and/or tape storage). Thus, memory 104 represents both main memory units, as well as long-term storage. Other types of memory may include biological memory.

Memory 104 may store program instructions and/or data on which program instructions may operate. By way of example, memory 104 may store these program instructions on a non-transitory, computer-readable medium, such that the instructions are executable by processor 102 to carry out any of the methods, processes, or operations disclosed in this specification or the accompanying drawings.

As shown in FIG. 1, memory 104 may include firmware 104A, kernel 104B, and/or applications 104C. Firmware 104A may be program code used to boot or otherwise initiate some or all of computing device 100. Kernel 104B may be an operating system, including modules for memory management, scheduling and management of processes, input/output, and communication. Kernel 104B may also include device drivers that allow the operating system to communicate with the hardware modules (e.g., memory units, networking interfaces, ports, and busses), of computing device 100. Applications 104C may be one or more userspace software programs, such as web browsers or email clients, as well as any software libraries used by these programs. Memory 104 may also store data used by these and other programs and applications.

Network interface 106 may take the form of one or more wireline interfaces, such as Ethernet (e.g., Fast Ethernet, Gigabit Ethernet, and so on). Network interface 106 may also support communication over one or more non-Ethernet media, such as coaxial cables or power lines, or over wide-area media, such as Synchronous Optical Networking (SONET) or digital subscriber line (DSL) technologies. Network interface 106 may additionally take the form of one or more wireless interfaces, such as IEEE 802.11 (Wifi), BLUETOOTH®, global positioning system (GPS), or a wide-area wireless interface. However, other forms of physical layer interfaces and other types of standard or proprietary communication protocols may be used over network interface 106. Furthermore, network interface 106 may comprise multiple physical interfaces. For instance, some embodiments of computing device 100 may include Ethernet, BLUETOOTH®, and Wifi interfaces.

Input/output unit 108 may facilitate user and peripheral device interaction with computing device 100. Input/output unit 108 may include one or more types of input devices, such as a keyboard, a mouse, a touch screen, and so on. Similarly, input/output unit 108 may include one or more types of output devices, such as a screen, monitor, printer, and/or one or more light emitting diodes (LEDs). Additionally or alternatively, computing device 100 may communicate with other devices using a universal serial bus (USB) or high-definition multimedia interface (HDMI) port interface, for example.

In some embodiments, one or more computing devices like computing device 100 may be deployed to support a server-based architecture. The exact physical location, connectivity, and configuration of these computing devices may be unknown and/or unimportant to client devices. Accordingly, the computing devices may be referred to as "cloud-based" devices that may be housed at various remote data center locations. Examples include public cloud networks such as AMAZON WEB SERVICES® and MICROSOFT® AZURE®.

Figure 2:
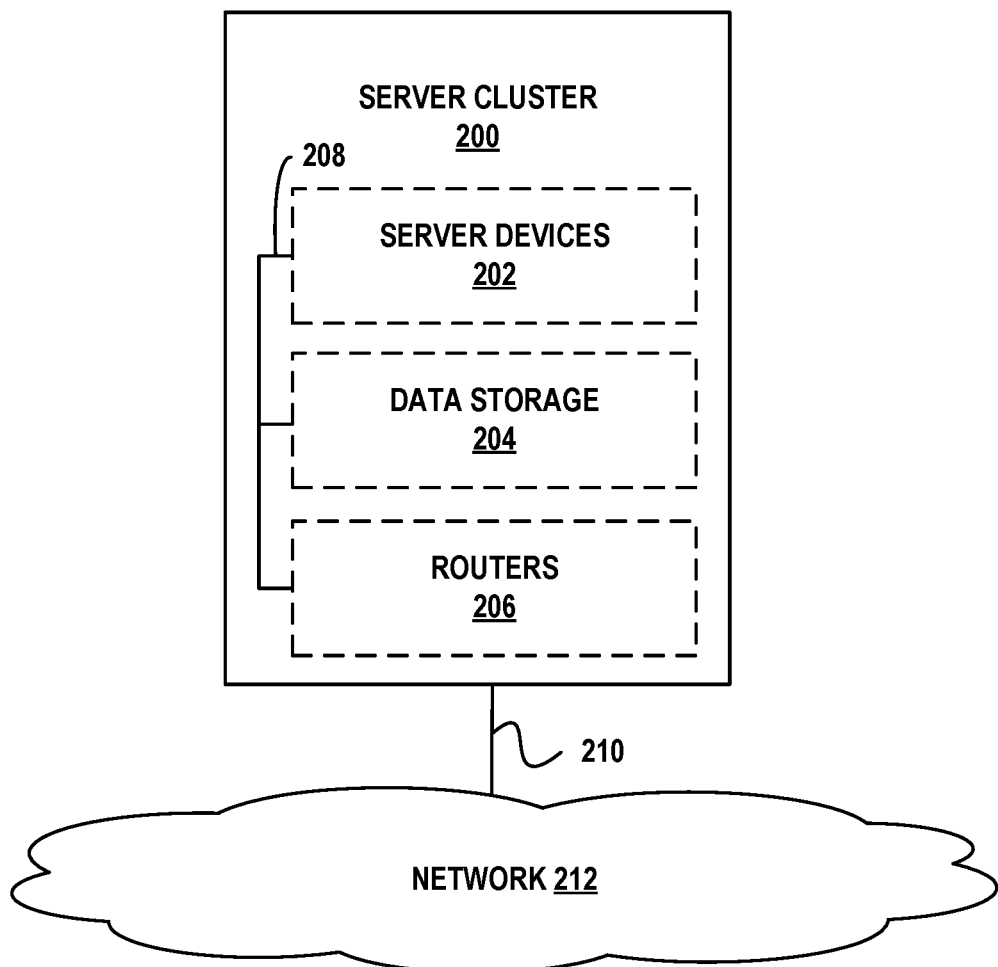
FIG. 2 illustrates a schematic drawing of a server device cluster, in accordance with example embodiments.

FIG. 2 depicts a cloud-based server cluster 200 in accordance with example embodiments. In FIG. 2, operations of a computing device (e.g., computing device 100) may be distributed between server devices 202, data storage 204, and routers 206, all of which may be connected by local cluster network 208. The number of server devices 202, data storages 204, and routers 206 in server cluster 200 may depend on the computing task(s) and/or applications assigned to server cluster 200.

For example, server devices 202 can be configured to perform various computing tasks of computing device 100. Thus, computing tasks can be distributed among one or more of server devices 202. To the extent that these computing tasks can be performed in parallel, such a distribution of tasks may reduce the total time to complete these tasks and return a result. For purpose of simplicity, both server cluster 200 and individual server devices 202 may be referred to as a "server device." This nomenclature should be understood to imply that one or more distinct server devices, data storage devices, and cluster routers may be involved in server device operations.

Data storage 204 may be data storage arrays that include drive array controllers configured to manage read and write access to groups of hard disk drives and/or solid-state drives. The drive array controllers, alone or in conjunction with server devices 202, may also be configured to manage backup or redundant copies of the data stored in data storage 204 to protect against drive failures or other types of failures that prevent one or more of server devices 202 from accessing units of data storage 204. Other types of memory aside from drives may be used.

Routers 206 may include networking equipment configured to provide internal and external communications for server cluster 200. For example, routers 206 may include one or more packet-switching and/or routing devices (including switches and/or gateways) configured to provide (i) network communications between server devices 202 and data storage 204 via local cluster network 208, and/or (ii) network communications between the server cluster 200 and other devices via communication link 210 to network 212.

Additionally, the configuration of routers 206 can be based at least in part on the data communication requirements of server devices 202 and data storage 204, the latency and throughput of the local cluster network 208, the latency, throughput, and cost of communication link 210, and/or other factors that may contribute to the cost, speed, fault-tolerance, resiliency, efficiency and/or other design goals of the system architecture.

As a possible example, data storage 204 may include any form of database, such as a structured query language (SQL) database. Various types of data structures may store the information in such a database, including but not limited to tables, arrays, lists, trees, and tuples. Furthermore, any databases in data storage 204 may be monolithic or distributed across multiple physical devices. The information stored in such a database (i.e., the information regarding potential experts described herein) may be updated in real time or on a periodic or irregular basis.

Server devices 202 may be configured to transmit data to and receive data from data storage 204. This transmission and retrieval may take the form of SQL queries or other types of database queries, and the output of such queries, respectively. Additional text, images, video, and/or audio may be included as well. Furthermore, server devices 202 may organize the received data into web page representations. Such a representation may take the form of a markup language, such as the hypertext markup language (HTML), the extensible markup language (XML), or some other standardized or proprietary format. Moreover, server devices 202 may have the capability of executing various types of computerized scripting languages, such as but not limited to Perl, Python, PHP Hypertext Preprocessor (PHP), Active Server Pages (ASP), JAVASCRIPT®, and so on. Computer program code written in these languages may facilitate the providing of web pages to client devices, as well as client device interaction with the web pages.

II. ENSEMBLE MODEL FOR DOCUMENT CLASSIFICATION

Figure 3:
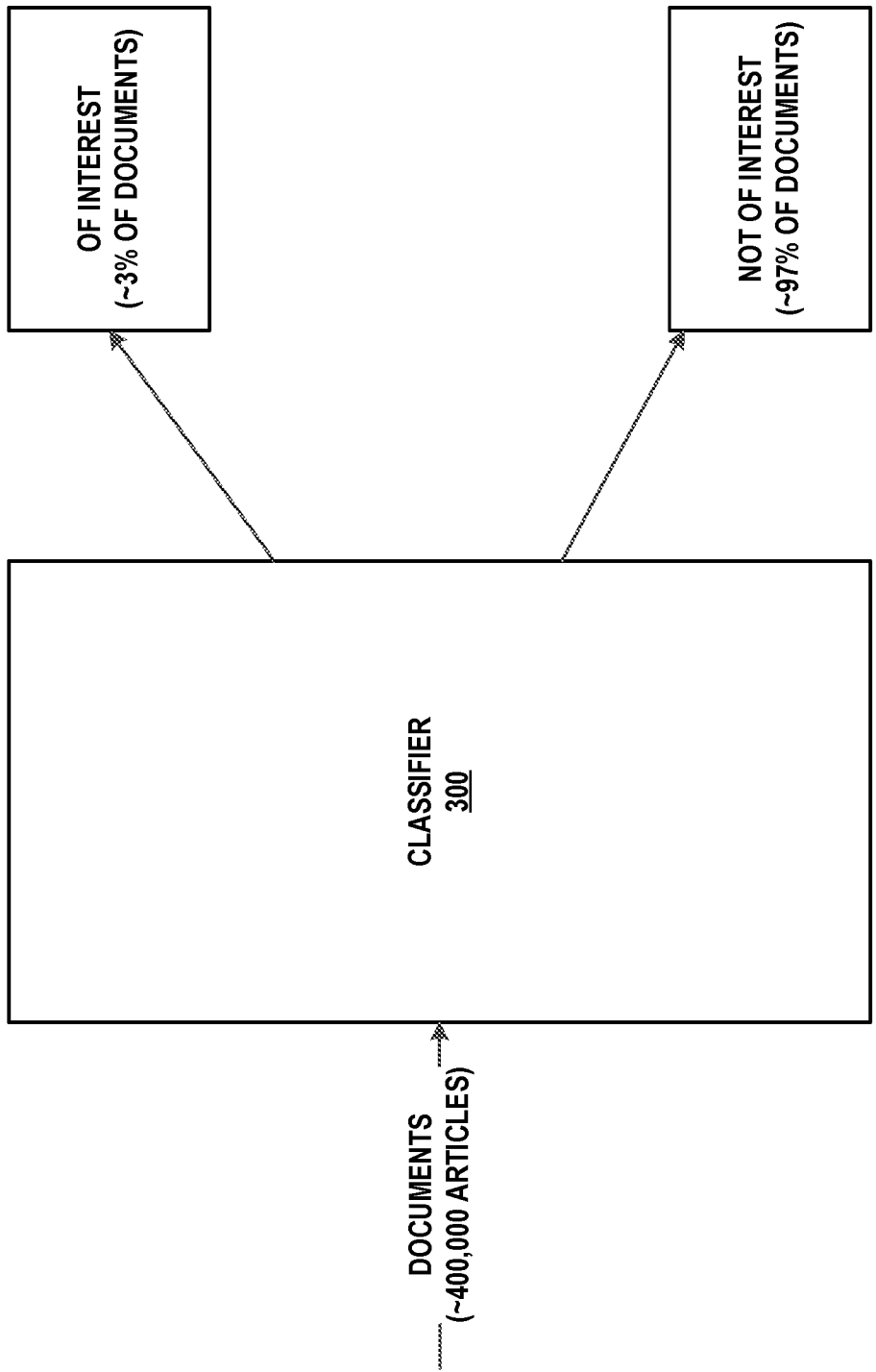
FIG. 3 depicts a classification model, in accordance with example embodiments.

As noted above, it is valuable to be able to automatically classify documents, such as articles in the scientific and medical literature, as either being of interest or not of interest with respect to safety signals of drug. In general, this process may be considered to be binary classification and is depicted in FIG. 3. A corpus of documents is provided to classifier 300, which in turn classifies each document as either being of interest or not of interest. Thus, classifier 300 may produce a binary output per document (e.g., a 1 indicating that the document is of interest or a 0 indicating that the document is not of interest). In some embodiments, classifier 300 may produce a probability per document indicating the likelihood that each document is of interest, and this probability may be mapped to a binary output by way of a threshold (e.g., probabilities greater than or equal to 50% are mapped to 1 and probabilities less than 50% are mapped to 0). Other possibilities exist.

In some embodiments, the binary classification described above may initially be a trinary classification into the categories of retain for interest (RFI), for further evaluation (FFE), and not of interest (NOI). The RFI category may include documents containing useful background information relating to a drug, but not requiring any immediate action (e.g., indications of off-label use, use by the elderly, or use by pregnant women, results of epidemiological studies, indications of targeted proteins, etc.). The FFE category may include documents containing a new safety signal (e.g., an unlisted adverse event) or when further evaluation is warranted due to product-specific or manufacturer-specific rules. In practice, however, the FFE category is often combined into the RFI category since the former is typically much smaller than the latter. As noted, the NOI category is for articles that do not include new safety signals or do not add to existing knowledge about a drug.

As shown in FIG. 3, classifier may be trained with a large number of documents (e.g., approximately 400,000 articles that were manually classified into ground truth binary values over the last 10 years). Of these, approximately 3% were determined to be of interest and approximately 97% were determined to be not of interest.

Figure 4:
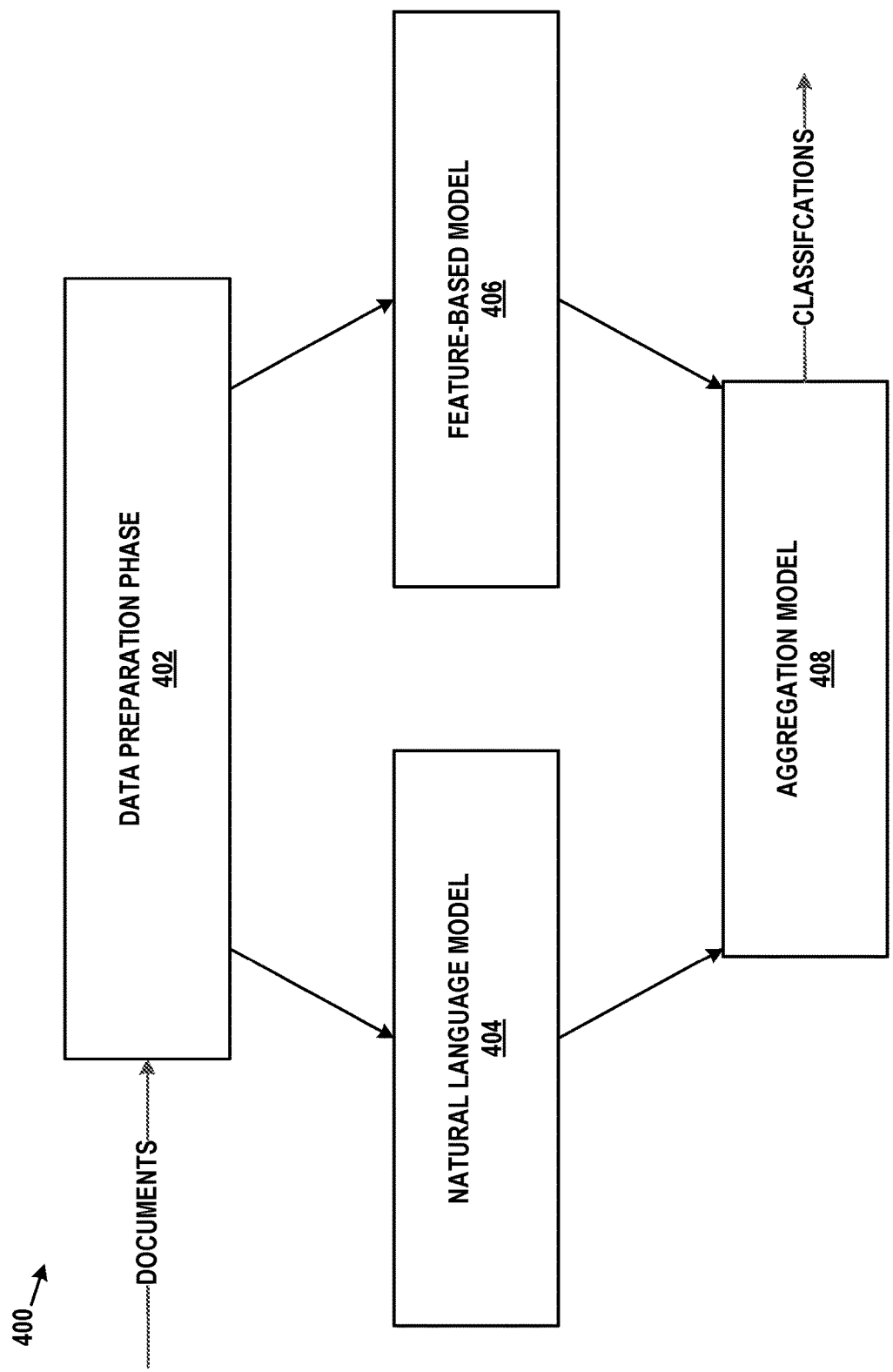
FIG. 4 depicts an ensemble-based classifier, in accordance with example embodiments.

Through extensive research and experimentation, it has been found that the performance of classifier 300 can be improved by using an ensemble model rather than any one particular classification model. An ensemble is a series of rules-based and/or learning models that, in aggregate, produce a result. FIG. 4 depicts such ensemble model 400 that can be used for safety signal detection in documents. Ensemble model 400 may be considered to be a more detailed depiction of the inner workings of classifier 300.

Particularly, the documents are provided to data preparation phase 402, and data preparation phase 402 transforms the documents and/or their associated metadata into a format that is compliant with input requirements of natural language model 404. Data preparation phase 402 may also perform feature extraction from the documents that can be provided as input to feature-based model 406.

Natural language model 404 uses a deep learning language construct that has been initially pre-trained on a generic corpus of documents. The documents provided as shown in FIG. 4 serve to fine-tune this training with domain-specific knowledge. This model, when the fine tuning is complete, automatically identifies features in the documents and classifies the documents based on these features.

Feature-based model 406 uses and/or is based on features identified by human reviewers that can be used to classify the documents. The documents provided, and features extracted therefrom, are used to train multiple classifiers, and the learning process involves identifying a combination of these classifiers that represent the feature most likely to produce an accurate classification.

Aggregation model 408 takes the classifications of the documents as produced by natural language model 404 and feature-based model 406, and maps them into overall classifications of each document. Aggregation model 408 may be trained based on outputs from each of natural language model 404 and feature-based model 406 that are mapped to ground-truth classifications in the labels of the documents.

A rationale for developing ensemble model 400, rather than a simpler model based on just one learning technique, is to provide improved classification performance but retain some degree of "explainability". Particularly, natural language model 404 can automatically develop its own set of "rules" without human intervention, but these rules are encoded as millions of weights in a set of layers that represent language knowledge. Thus, it is practically impossible to determine, from these weights, why a particular article was classified into one category or another. On the other hand, feature-based model 406 identifies the features that are most likely to drive classification accuracy. But lacking a language model, feature-based model 406 will be unable to identify some types of feature co-occurrences that can be learned by natural language model 404. By combining these techniques, ensemble model 400 is designed to produce classifications that are both accurate and explainable.

Since each part of ensemble model 400 involves a number of operations and some degree of complexity, these parts are described in more detail below.

A. Data Preparation

Figure 5:
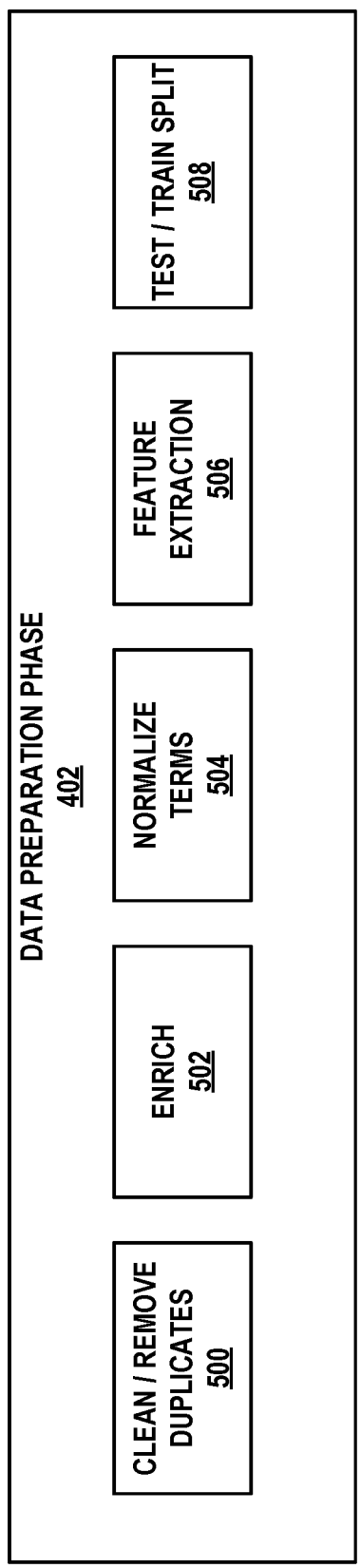
FIG. 5 depicts a data preparation phase, in accordance with example embodiments.

As noted, data preparation phase 402 involves organizing and transforming data representing documents into a form that can be processed effectively by natural language model 404 and feature-based model 406. This is depicted in FIG. 5 as five distinct steps: clean/remove duplicates 500, enrich 502, normalize terms 504, feature extraction 506, and test/train split 508. More or fewer steps may be present.

In addition to the documents, a manually curated set of drug-specific terms may be developed. These terms may include, for each drug, one or more keep under review (KUR) terms, a list of adverse events associated with the drug, and general designated medical events (DMEs) that may be considered to be adverse.

The documents provided as input to data preparation phase 402 include articles from the scientific and/or medical literature, for example, potentially accompanied by metadata representing key characteristics of these document. Key characteristics may include title, author, abstract, and a list of keywords (e.g., provided by the publisher). In some cases, processing in various parts of data preparation phase 402 is carried out on the documents, their metadata, or both. For purposes of training, each document may also be associated with a labelled classification (i.e., of interest or not of interest) manually assigned by reviewers. The combination of a document, its metadata, and its label may be referred to as an entry within the training corpus.

Notably, data preparation phase 402 may contain more or fewer steps, and may carry out these steps in different orders. Thus, the embodiments of data preparation phase 402 described herein are merely for purposes of example.

1. Clean/Remove Duplicates

Clean/remove duplicates 500 step may involve placing the entries in a common format and removing duplicate entries. Duplicate entries may be detected as, for example, documents with the same authors and title. In some cases, multiple entries for the same document may exist, each associated with different subsets of metadata. In these cases, the de-duplication process may include merging the metadata from different entries of the same document.

2. Enrich

Enrich 502 step may involve looking up one or more documents in a database and obtaining further metadata for these documents. As an example, a published article may be looked up in EMBASE®, a curated database with records of over 30 million publications in the biomedical and pharmacological fields. The articles in the database may have associated therewith a list of curated keywords or other metadata that can be incorporated into the entry containing the article. Other databases that can be used for this purpose include Insightmeme. A result of enrich 502 step is that the corpus of documents may include more metadata and/or more accurate metadata.

3. Normalize Terms

Normalize terms 504 step may involve mapping terms in the documents that are synonymous into a common form. For example, sometimes drugs are referred to by their brand names, generic names, chemical makeup, or some other identifier. With reference to a database of drug names, these different names for each drug are normalized into one per drug. For example, the drug generic names amphetamine and dextroamphetamine may refer to drugs with the brand names of Adderall, Adderall XR, and Mydayis. These five names may all be mapped to the term "dextroamphetamine" for example. Doing so may involve use of a named entity recognition (NER) tool, such as TERMite.

4. Feature Extraction

Feature extraction step 506 involves identifying features in each document. These features may include drug names, genes, medical conditions, and so on. This may also involve use of an NER tool, such as TERMite. The NER tool may identify each term (feature) within the text of a document and/or its metadata, and produce a list of such terms, their type, a link to a structured database describing the term, and/or a reference to a section or sentence within the document containing the term.

As an example, suppose the 23rd and 24th sentences of a document contains the following text: "This study evaluated the efficacy and safety of DPP4 inhibitor saxgliptin in patients with type 2 diabetes. Incidence of hypoglycaemia with saxagliptin was compared to placebo." The NER tool may identify that DPP4 is a gene, that saxgliptin is a drug, and that type 2 diabetes and hypoglycaemia are medical conditions.

As an example, the NER tool may produce output for the document similar to table 600 of FIG. 6A. Each feature is categorized into a type (e.g., drug, gene, or medical condition), a name, an identifier or ID (e.g., a label from a medical or chemical database), a reference to a description of the feature (e.g., a URL or search query for a database), and the sentence(s) in which the feature appears. This output may be provided to natural language model 404 and/or feature-based model 406 and used as described below.

In more detail, additional data and reviewer decision logic was used to develop approximately 50 features which were judged to be potentially useful in deciding on a document's classification. The full list 610 is provided in FIG. 6B. Additional features may be created using the approach outlined by Wu and He in *Enriching Pre-trained Language Model with Entity Information for Relation Classification* (2019). Specifically, this approach can be used to identify causal relationships between drugs and KUR terms by training on a set of sentences containing both a drug and a KUR term. The sentences were labeled as either containing a causal link or no causal link between the drug and KUR term. The resulting classifier was used to generate a feature to be included in the model.

Adverse event terms and statistical terms were extracted using TERMite. Particularly, adverse event terms from the MedDRA database and their synonyms were identified in the documents. For selected drugs, indication terms were extracted from the relevant CDS section using the same technique and removed. Historical KUR and listed terms were mapped to adverse event terms extracted with TERMite based on the document review date occurring after the term start date and before the term end date (if specified). Special populations were identified using a combination of TERMite MedDRA entities and manually added terms. These included age-related terms (such as "elderly") and pregnancy-related terms. Drug names were identified in the text using a list of synonyms. Citescore metrics were mapped to journal names extracted from full citations of articles (excluding conference abstracts). The earliest available Citescore metrics from 2011 were also mapped to articles with review years prior to 2011.

Ultimately, feature extraction step 506 may produce, for each document, an array of binary indicators, one for each of the features in list 610. If the feature is present in the document, the associated indicator is a 1, while if the feature is not present in the document, the associated indicator is a 0.

5. Test/Train Split

Test/train split 508 step may involve preparing for training ensemble model 400 by splitting the entries into a training set and a testing set. Typically this would be approximately an 80/20 split, with 80% of the entries used for training and 20% used for testing. But other percentages may be used. Once ensemble model 400 is trained with the training set, the testing set may be used to evaluate the efficacy of ensemble model 400.

B. Natural Language Model

Turning back to FIG. 4, natural language model 404 may include a pre-trained language model that is then fine-tuned with the domain-specific training data from data preparation phase 402. The pre-trained language model may be a variation of the Bidirectional Encoder Representations from Transformers (BERT) model, for example. Pre-trained versions of BERT consist of a number of weights (e.g., over 100 million) that define a stack of deep learning layers representing contextual language knowledge. These weights were derived by training BERT, possibly in an unsupervised fashion, on a vast corpus of language samples from WIKI-PEDIA® and other databases. As a result, BERT has a significant contextual understanding of the vocabulary, grammar, and usage of a language (e.g., English). Pre-trained BERT models can be used largely as-is for various tasks, such as predicting the next word in a sequence of words and whether, for a given pair of sentence, one sentence follows the other.

Various pre-trained BERT models have been developed for different domains. For example, SciBERT uses the BERT structure, but was trained with text from over one million scientific papers. BioBERT also uses the BERT structure, but combines the BERT training corpus with abstracts and articles from the PubMed database. In tests, both SciBERT and BioBERT outperform standard BERT on natural language understanding tasks from their respective domains.

Once a pre-trained BERT model is selected, it can be structured and fine-tuned for a specific task. This may involve adding one or more further layers (e.g., classification layers) to the model and/or further training the model as modified in a supervised fashion with additional labelled data set related to the task. Typically, the additional data set is much smaller than the corpus used to pre-train the BERT model. As a consequence, the further training of the fine-tuning step is typically much faster than the pre-training (e.g., hours versus days).

A difference between BERT-based models and previous word embedding models is that the former is contextual (based on surrounding words) while the latter is context-free. Put another way, a BERT may represent a word with a number of different vectors, one for each context in which the word is used in the training data. Prior word embedding models determine a single vector mapping for all uses of the word regardless of context.

Figure 7:
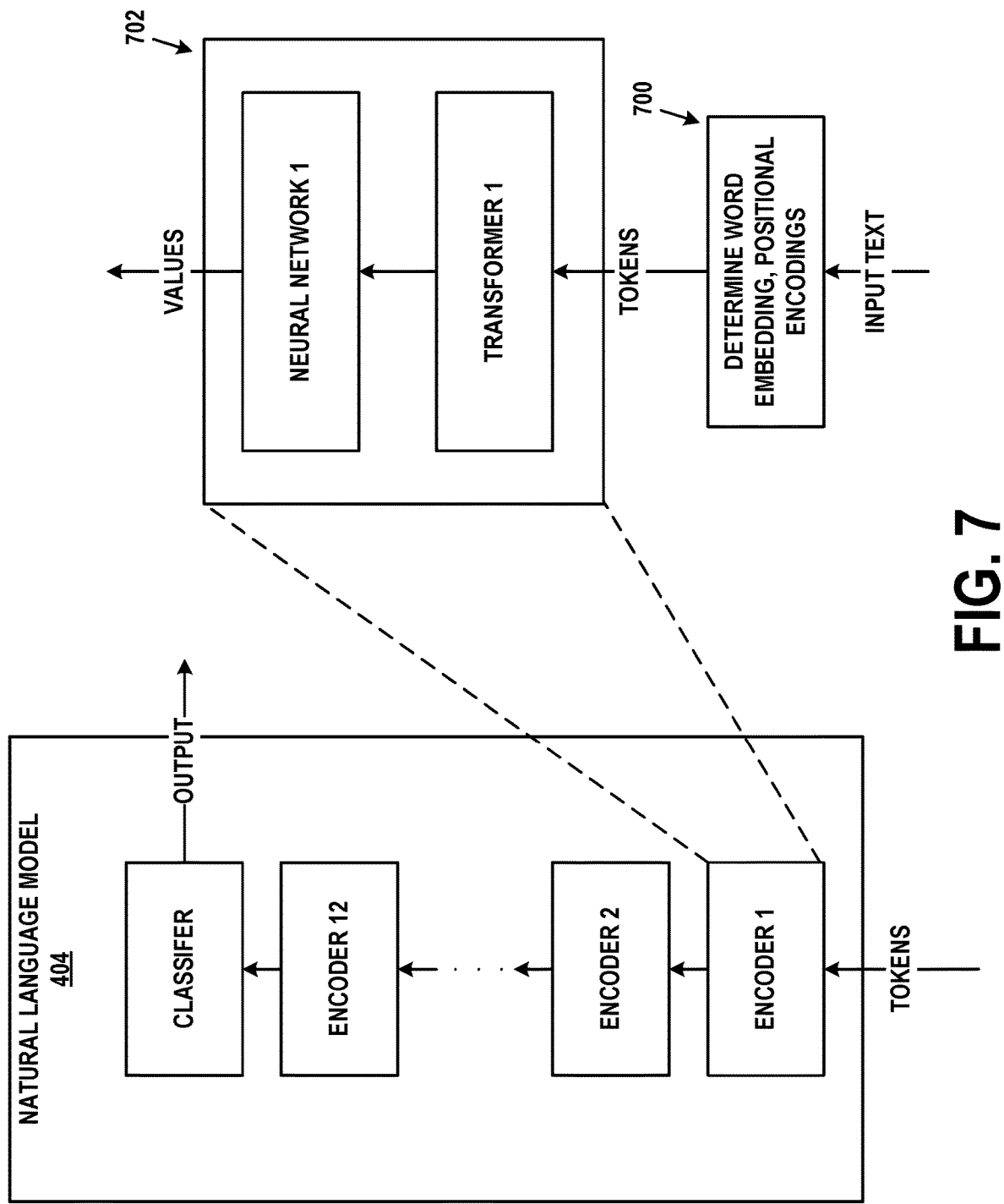
FIG. 7 depicts a natural language model, in accordance with example embodiments.

FIG. 7 depicts the architecture of natural language model 404, which is assumed to be based on BERT. Particular, natural language model 404 includes a stack of encoders and a classifier. In FIG. 7, 12 encoders are present, but the embodiments herein may employ more or fewer encoders. Tokens representing input text are provided to encoder 1, and then progress takes place in series through encoder 2, encoder 3, and so on until encoder 12 is traversed. After encoder 12, the values produced thereby are provided to a classifier that predicts whether the input text contains a safety signal.

Blocks 700 and 702 show input text processing and encoder 1 in more detail. Input text may be one or more sentences of a document. Block 700 transforms this input text into tokens. In particular, a word embedding may be used to map each word in the input text to a vector in n-space, wherein the values of the vector represent a semantic meaning of the word. This mapping may be pre-determined and could have been developed based training an encoder using word vectors (e.g., with the word2vec software package), or may be learned dynamically during the training of natural language model 404.

As an example suppose that the input text is "Hello, how are you?" Tokenized, this text becomes the array ["Hello", ",", "how", "are", "you", "?"]. Then each token is transformed into a pre-determined (and for all intents and purposes, arbitrary) number. For example, numericalization of the array could result in [34, 90, 15, 684, 55, 193]. Then, each of these numbers is used as an index to look up the associated word embedding in a database E. For instance, considering just the number representing "Hello", this could result in an n-dimensional vector of E[34]=[123.4, 0.32, . . . 94, 32]. The overall result is a matrix of n-dimensional vectors, one representing each token derived from the input text. These vectors may be considered to be an expanded version of the tokenized representation of the input text.

Additionally, a positional encoding may be added to the vector representation of each word to indicate its location in the input text. These locations may be absolute or relative, and seek to modify the embedded semantic meaning of a word based on where it appears in the input text. This allows the upstream encoders to understand and take into account the notion that positional relationships between words in a sentence can have an impact on their contextual meaning. For example, given a sentence containing the term "river bank" and another sentence containing the term "bank robber", it should be clear that the meanings of the word "bank" in these sentences are quite different. With positional encodings, natural language model 404 would be able to differentiate between these two meanings.

In some embodiments, special tokens may be added to the tokens representing the input text. These special tokens may provide additional instructions or information to natural language model 404, such as that a classification task is being carried out, or a delimiter exists between two parts of the input text (e.g., between two sentences).

Block 702, representing encoder 1, receives the tokens and passes them through two modules, a transformer and a neural network. The transformer uses a set of trained matrices on the tokens to determine relationships between pairs of words in the input text. More precisely, each individual word may be represented as a centroid of projected vectors through a matrix representing these relationships. This process can be repeated a number of times to determine multiple relationships between words in the input text. Ultimately, the output of the transformer may be considered to be a concatenation of these resulting centroids.

This output may be provided to the neural network. In some embodiments, an extent of normalization may be applied to the output before it is introduced to the neural network.

The neural network may take on a variety of forms. One possible implementation is a three-layer network, with a rectified linear activation unit (RELU) layer between two fully-connected layers. The RELU layer applies the RELU function to its inputs, where the RELU function is defined as $RELU(x)=\max(0, x)$. The RELU layer may have a different number of nodes as the fully-connected layers. Using the neural network may enrich the representation generated by the transformer.

The output values of the neural network may serve as the output values of the encoder. In some embodiments, a further extent of normalization may be applied to this output as well before it is introduced to the next encoder.

To that point, the output of encoder i is provided as the input to encoder i+1. Thus, aside from encoder 1 which takes tokens are input, each encoder takes values from its previous encoder as input.

Natural language model 404 also includes a classifier that receives the output values of encoder 12 as its input, and produces a classification of the input text as a final result. This classification may be a binary value indicating whether the input text is predicted to contain a safety signal, or a probability representing a likelihood that the input text contains a safety signal.

To facilitate this process, a document (e.g., a medical or scientific article) may be broken up into title, abstract and keywords. The title and keyword sections are always included in the model input. When the total length exceeds 512 tokens (e.g., the limit for BERT models) only the start and the end of the abstract is included as input. Experiments were run by dividing documents in different ways and the method above led to the best performances. However, to get around the token limit of the BERT models, LONG-FORMER or similar techniques could be used. The embodiments herein allow modules including these techniques to be plugged into the overall model.

C. Feature-Based Model

Feature-based model 406 may be, for example, a gradient-boosting tree model using the feature data extracted from the documents in accordance with list 610. Such a model, in general, consists of three main components: a loss function, learning sub-models based on decision trees that make predictions, and an additive sub-model to add learning sub-models in order to minimize the loss function.

The loss function should be differentiable so that it can operate on a gradient. Various types of loss functions are possible, including mean squared error and logarithmic loss.

A decision tree is a branching arrangement of questions about a document that, when answered, result in a prediction of whether the document is of interest. A decision tree can be constructed in an iterative or recursive fashion. In short, a decision tree maps the values of input features to values of output characteristics using a tree-like structure. Branching points can be found in a greedy fashion based on the entropy or Gini index of the training data. Branches that are most likely to direct the traversal toward relevant features are placed higher in the tree. In practical embodiments, the depth, number of splits per node, or total number of leaf nodes may be constrained so that each tree is more tractable. Using randomization or by varying parameters, multiple decision trees may be generated for a given data set.

The additive sub-model is used to add together results from subsets of the decision trees so that the loss function is minimized. After calculating the loss for a given subset of tree, the gradient descent procedure involves adding a new tree to the model that reduces the loss (i.e., follows the gradient). This can be accomplished by parameterizing the tree, then modifying the parameters of the tree and moving in the right direction by reducing the residual loss.

As a simplified example, FIG. 8 provides two decision trees that could be used in the feature-based model. Features F1, F2, F3, F4, and F5 are represented as the nodes of the trees. In tree 800, all features are present, but in tree 802 feature F2 is omitted.

Trees 800 and 802 can be interpreted as follows. There are two edges extending from each node, one labelled "yes" and the other labelled "no". If the feature represented by the node is present in a document, the "yes" edge is traversed, and if the features represented by the node is not present in the document, the "no" edge is traversed. All leaf nodes are labelled with binary values, 0 or 1. Upon traversal of a tree for a given document, the value of leaf node that is reached represents whether the document is of interest (the leaf node has a value of 1) or not (the leaf node has a value of 0).

As an example, suppose that features F 1 and F3 are present in a document, but features F2 and F4 are not. Then, traversal of tree 800 will include the nodes labelled with F1 and F2. From the node labelled with F2, the "no" edge will be taken, resulting in an output of 1 (that the document is of interest). A traversal of tree 802 will include the nodes labelled with F3, F1, and F4. From the node labelled with F4, the "no" edge will be taken, resulting in an output of 0 (that the document is not of interest).

As described above, the results from a number of these trees can be added together so that the loss function is minimized, then a new tree further reducing the loss function may be generated. This process continues for some number of iterations until the results converge.

D. Aggregation Model

Figure 9:
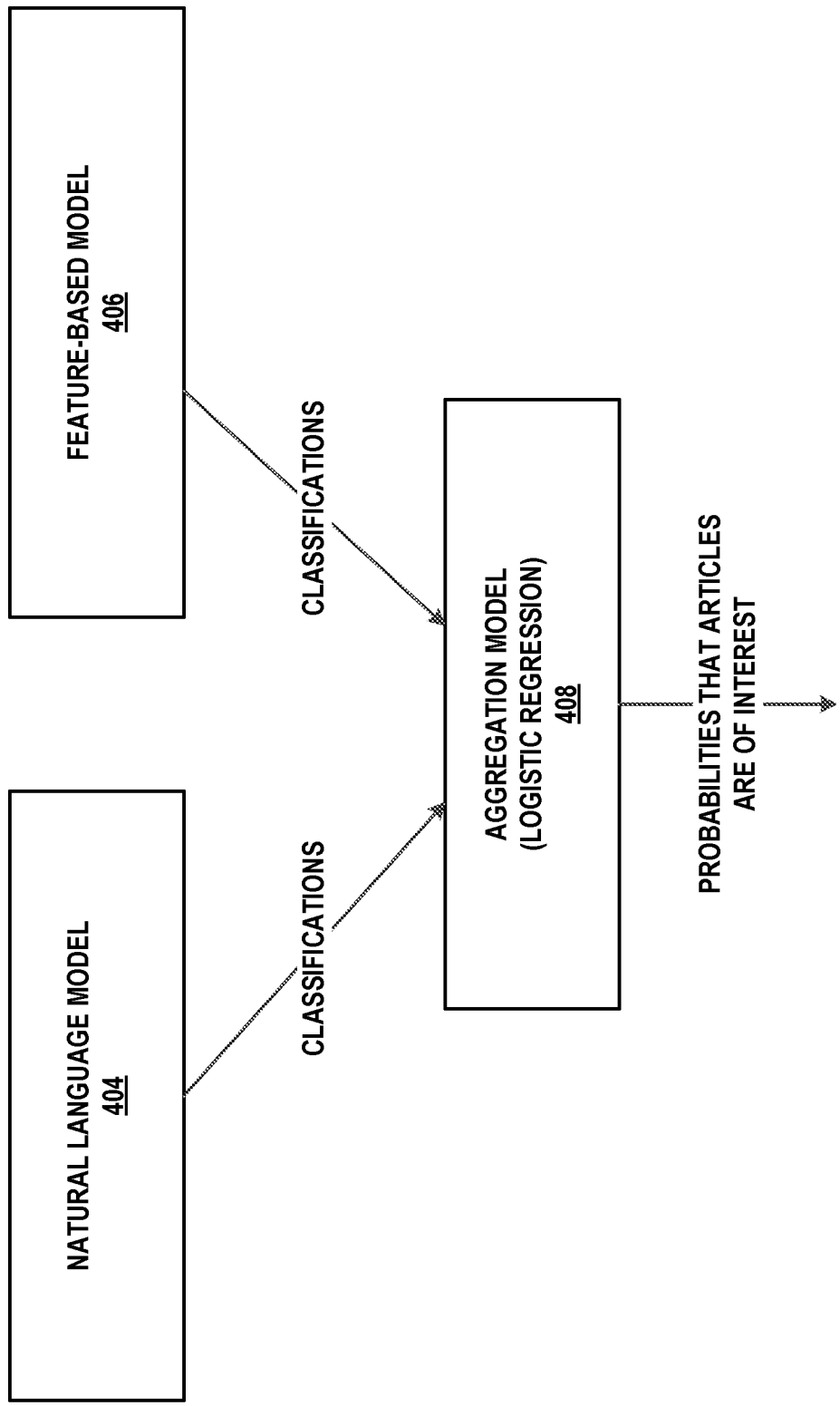
FIG. 9 depicts an aggregation model, in accordance with example embodiments.

Turning back to FIG. 4 once again, aggregation model 408 takes as input the classifications produced by each of natural language model 404 and feature-based model 406 for a given article, and produces a final classification of whether than article is of interest. FIG. 9 expands upon this section of FIG. 4 and describes one possible aggregation model using multivariate logistic regression.

Notably, the classifications produced by natural language model 404 and feature-based model 406 may be binary (e.g., 0 indicating that an article is not of interest and 1 indicating that an article is of interest) or probabilistic (e.g., taking on a value between 0.0 and 1.0 inclusive that represents the probability that an article is of interest). Further, while the aggregate classifications produced by aggregation model 408 are shown as probabilities, these classifications can easily be transformed into binary values through use of thresholding.

As noted, aggregation model 408 is assumed to be based on multivariate logistic regression, though other techniques can be used. Put in concrete terms, the log-odds 1 of an outcome p=P(Y=1) for a output variable Y can be modeled with a logistic function over independent variables $x_1$ and $x_2$ as:

$$l = \ln\frac{p}{1-p} = \beta_0 + \beta_1 x_1 + \beta_2 x_2$$

Thus, the probability that Y=1 can be written as:

$$p = \frac{1}{1 + e^{-(\beta_0 + \beta_1 x_1 + \beta_2 x_2)}}$$

Once the values for $\beta_i$ are found, the probabilities that Y=1 and Y=0 is easily derived. The values for $\beta_i$ are found from performing a maximum likelihood estimation on the training data (e.g., example outputs from natural language model 404 and feature-based model 406). This may entail, for example, using an iterative process, such as Newton's method, until the values converge.

To select the threshold above which a predicted probability is classified as of interest (RFI or FFE), Neyman-Pearson Classification is used. Specifically, the "umbrella algorithm" of Tong, Feng, and Li may be used. This provides a guarantee that, with a pre-specified high probability (1−δ), there is a pre-specified lower bound (1−α) on the population sensitivity. Furthermore, upper and lower bounds are calculated for the population specificity and FFE sensitivity, with each bound holding with high probability (1−δ). Note that the guarantee is on recall/sensitivity of documents of interest, including those classified as RFI. With a higher number of FFE samples, a guarantee on FFE sensitivity could be provided directly. In some experiments, if 158 such documents are used for threshold calibration, then a guarantee of at most 98% sensitivity at 95% probability could be provided.

This allows the model to be tuned to balance the sensitivity and specificity. It also provides robustness of the predicted error rate for the classifier across the whole population. This is important in the application of the model to pharmacovigilance, where obtaining high recall with confidence is desirable.

III. EXPERIMENTAL RESULTS

The performance of the models were evaluated based on metrics including precision, sensitivity (recall), specificity, and f1. Each of these metrics are described below for classification tasks.

Precision is the number of true positives divided by the sum of the true positives and false positives, or tp/(tp+fp). It represents the fraction of correct positive classifications among all positive classifications. For the document classification task, precision represents the fraction of documents that were correctly classified as of interest out of all documents classified as of interest.

Sensitivity is the number of true positives divided by the sum of the true positives and false negatives, or tp/(tp+fn). It represents the fraction of correct positive classifications among the correct positive classifications and the incorrect negative classifications. For the document classification task, sensitivity represents the fraction of documents that were correctly classified as of interest out of all documents correctly classified as of interest and those that should have been classified as of interest but were not.

Specificity is the number of true negatives divided by the sum of the true negatives and false positives, or tn/(tn+fp). It represents the fraction of correct negative classifications among the correct negative classifications and the incorrect positive classifications. For the document classification task, sensitivity represents the fraction of documents that were correctly classified as not of interest out of all documents correctly classified as not of interest and those that should have been classified as not of interest but were not.

The f1 score can be calculated as the harmonic mean of the precision and sensitivity, or tp/(tp+0.5(fp+fn)), and measures the accuracy of classification. The highest possible f1 score is 1, indicating ideal precision and sensitivity, and the lowest possible value is 0 when either precision or sensitivity is 0.

Natural language model 404 was trained on a balanced set of approximately 10,000 randomly selected documents for each of the two classes—of interest and not of interest. Testing was done using this trained model on a balanced set of approximately 4,000 documents, including samples of interest and not of interest. The results are below.

|  | f1* | Precision* | Sensitivity | Specificity |
|---|---|---|---|---|
| Deep Learning | 0.35 | 0.25 | 0.87 | 0.80 |

The same test set of approximately 4,000 documents which was used for the natural language model 404 testing was set aside for testing feature-based model 406. A gradient-boosting classifier was then trained on all the remaining articles (approximately 400,000). The results are below.

|  | f1* | Precision* | Sensitivity | Specificity |
|---|---|---|---|---|
| Manual Features | 0.38 | 0.25 | 0.78 | 0.84 |

Feature-based model 406 also produced a listing of the five most important features in terms of their relevance to classification:

|  | Percentage importance |
|---|---|
| Drug | 33.26% |
| time_in_review | 18.51% |
| kur_abstract | 12.93% |
| drug_title | 7.45% |
| citescore | 4.75% |

Testing of the full classifier was performed on a subset of 197 articles corresponding to 5 pre-selected drugs, as well as the previous test set of 4,000 articles. The results are below.

|  | f1* | Precision* | Sensitivity | Sensitivity on FFE | Specificity |
|---|---|---|---|---|---|
| Ensemble (5 drugs) | 0.45 | 0.30 | 0.93 | 1.00 | 0.84 |
| Ensemble (all drugs) | 0.38 | 0.24 | 0.91 | 0.88 | 0.80 |
| Deep Learning (all drugs) | 0.35 | 0.25 | 0.87 | — | 0.78 |
| Manual Features (5 drugs) | 0.38 | 0.25 | 0.78 | — | 0.84 |

The full dataset was split into a training and validation sets using a random, un-stratified 70/30 split, and the natural language and features-based models were trained independently on the training set. This validation was in turn split randomly 80/20 for training and evaluating the ensemble. On this final evaluation set, high-probability (95%) bounds were calculated for specificity and FFE sensitivity given varying (high-probability) lower bounds on overall sensitivity. Note that the 95% probability holds independently for each bound, so the probability of both upper and lower bounds holding is 90%.

|  |  | 0.9 | 0.968 | 0.99 | 0.9968 | 0.999 | 0.99968 |
|---|---|---|---|---|---|---|---|
| NATURAL LANGUAGE | NA | 0.691, 0.704 | 0.443, 0.456 | 0.254, 0.267 | 0.211, 0.222 | 0.211, 0.222 | 0.211, 0.222 |
|  | FFE | 0.851, 0.998 | 0.905, 1.000 | 0.905, 1.000 | 0.905, 1.000 | 0.905, 1.000 | 0.905, 1.000 |
| MANUAL FEATURES | NA | 0.601, 0.614 | 0.382, 0.395 | 0.209, 0.220 | 0.152, 0.162 | 0.152, 0.162 | 0.152, 0.162 |
|  | FFE | 0.761, 0.972 | 0.851, 0.998 | 0.905, 1.000 | 0.905, 1.000 | 0.905, 1.000 | 0.905, 1.000 |
| ENSEMBLE | NA | 0.761, 0.773 | 0.494, 0.508 | 0.277, 0.289 | 0.233, 0.245 | 0.233, 0.245 | 0.233, 0.245 |
|  | FFE | 0.851, 0.998 | 0.905, 1.000 | 0.905, 1.000 | 0.905, 1.000 | 0.905, 1.000 | 0.905, 1.000 |

A goal of the embodiments herein was to demonstrate the potential to reduce the number of articles for manual review by removing false positives while maintaining a high level of specificity. The results show that this can indeed be achieved.

The overall results were comparable to those from inter-reviewer comparison and, importantly, the level of recall was higher (0.93 vs 0.83). The deep learning based language model, Scibert, gave the best performance, achieving good levels of both recall and specificity. Combining natural language with manual features improved the overall performance, particularly on recall. The analysis of misclassified articles was used during the development to improve the features and performance. This means even better performance over time by continuing the error analysis can be expected. The use of language features can help with "explainability" of the classifiers and could be used to let reviewers set their own specific strategies and highlighting. Both the natural language and the features-based models can be expected to improve over time by using reviewer feedback and additional training data.

IV. EXAMPLE OPERATIONS

Figure 10:
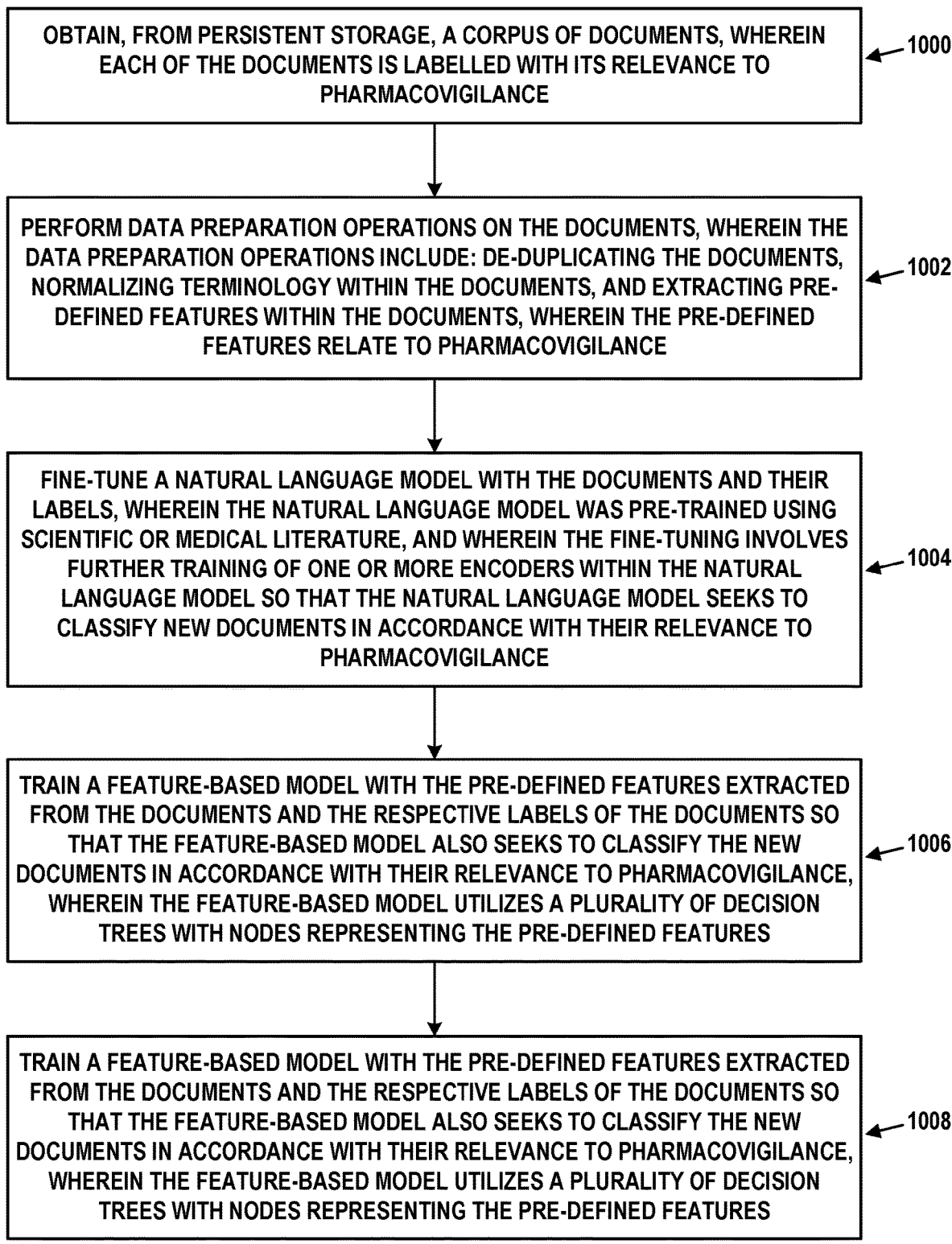
FIG. 10 is a flow chart, in accordance with example embodiments.
Figure 11:
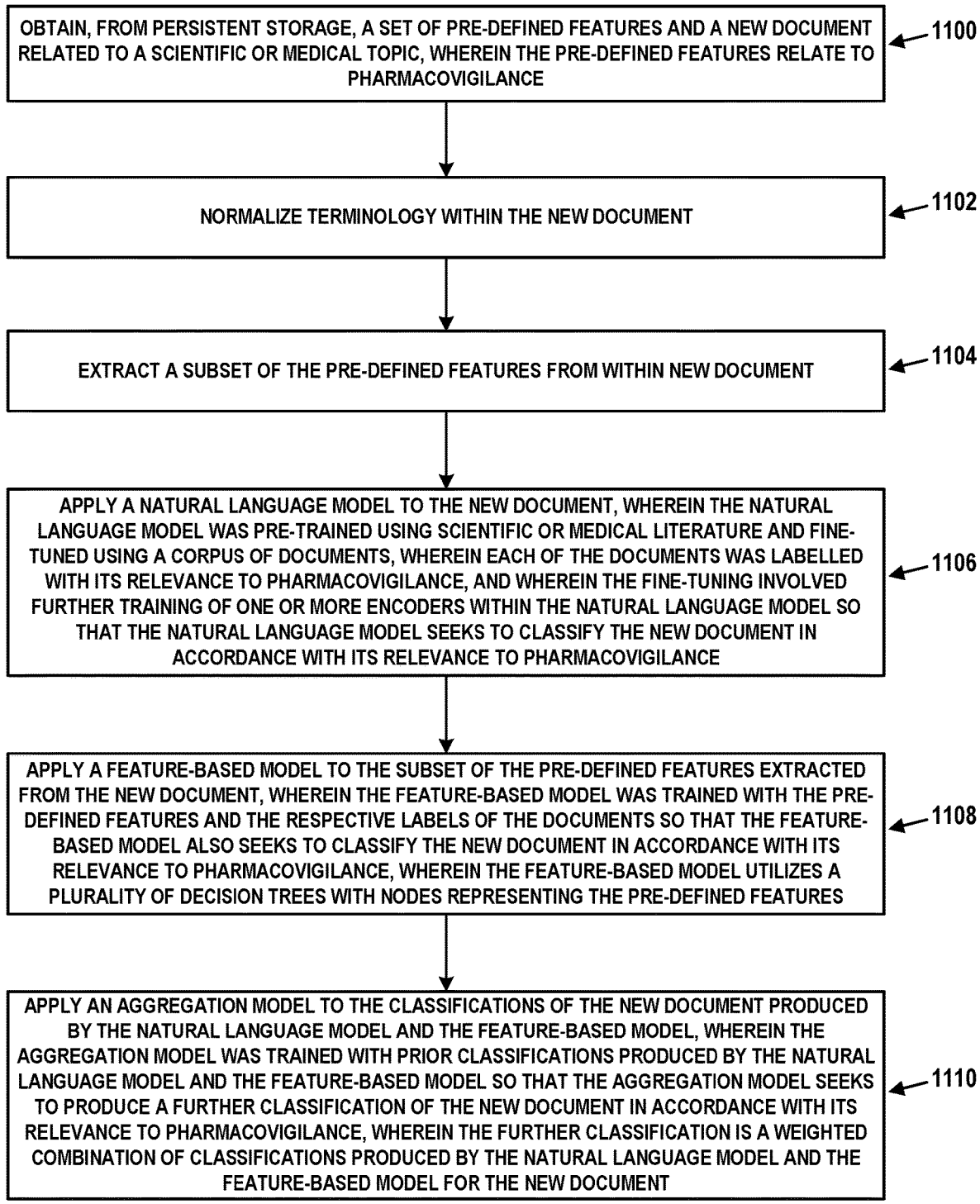
FIG. 11 is another flow chart, in accordance with example embodiments.

FIGS. 10 and 11 are flow charts illustrating example embodiments. The processes illustrated by FIGS. 10 and 11 may be carried out by a computing device, such as computing device 100, and/or a cluster of computing devices, such as server cluster 200 or computational instance 322. However, the processes can be carried out by other types of devices or device subsystems.

The embodiments of FIGS. 10 and 11 may be simplified by the removal of any one or more of the features shown therein. Further, these embodiments may be combined with one another, as well as features, aspects, and/or implementations of any of the previous figures or otherwise described herein.

Block 1000 of FIG. 10 may involve obtaining, from persistent storage, a corpus of documents, wherein each of the documents is labelled with its relevance to pharmacovigilance.

Block 1002 may involve performing data preparation operations on the documents, wherein the data preparation operations include: de-duplicating the documents, normalizing terminology within the documents, and extracting pre-defined features within the documents, wherein the pre-defined features relate to pharmacovigilance.

Block 1004 may involve fine-tuning a natural language model with the documents and their labels, wherein the natural language model was pre-trained using scientific or medical literature, and wherein the fine-tuning involves further training of one or more encoders within the natural language model so that the natural language model seeks to classify new documents in accordance with their relevance to pharmacovigilance.

Block 1006 may involve training a feature-based model with the pre-defined features extracted from the documents and the respective labels of the documents so that the feature-based model also seeks to classify the new documents in accordance with their relevance to pharmacovigilance, wherein the feature-based model utilizes a plurality of decision trees with nodes representing the pre-defined features.

Block 1008 may involve training an aggregation model with classifications produced by the natural language model and the feature-based model so that the aggregation model seeks to produce further classifications of the new documents in accordance with their relevance to pharmacovigilance, wherein the further classifications are weighted combinations of classifications produced by the natural language model and the feature-based model for the new documents.

In some embodiments, at least some of the documents are from the scientific or medical literature.

In some embodiments, each respective selection within the documents is labelled with a binary value indicating that the selection is either of interest or not of interest to pharmacovigilance.

In some embodiments, the relevance to pharmacovigilance for each of the documents is expressed with a binary value indicating that each of the documents is either of interest or not of interest to pharmacovigilance.

In some embodiments, the relevance to pharmacovigilance for each of the documents is expressed with a probability that each of the documents is of interest to pharmacovigilance.

In some embodiments, the natural language model is a context-free word embedding model.

In some embodiments, the encoders of the natural language model each contain a transformer and a neural network.

In some embodiments, the pre-defined features include terms related to drugs, statistical characteristics, risk scores, designated medical events, adverse medical events, and terms pre-selected to keep under review.

In some embodiments, the pre-defined features also include indications of combinations of the terms appearing a common sentence or consecutive sentences.

In some embodiments, the feature-based model is a gradient-boosting model.

In some embodiments, the aggregation model applies multivariate logistic regression to produce the further classifications.

Some embodiments may involve storing, in the persistent storage, the natural language model, the feature-based model, and the aggregation model as trained.

Block 1100 of FIG. 11 may involve obtaining, from persistent storage, a set of pre-defined features and a new document related to a scientific or medical topic, wherein the pre-defined features relate to pharmacovigilance.

Block 1102 may involve normalizing terminology within the new document.

Block 1104 may involve extracting a subset of the pre-defined features from within new document.

Block 1106 may involve applying a natural language model to the new document, wherein the natural language model was pre-trained using scientific or medical literature and fine-tuned using a corpus of documents, wherein each of the documents was labelled with its relevance to pharmacovigilance, and wherein the fine-tuning involved further training of one or more encoders within the natural language model so that the natural language model seeks to classify the new document in accordance with its relevance to pharmacovigilance.

Block 1108 may involve applying a feature-based model to the subset of the pre-defined features extracted from the new document, wherein the feature-based model was trained with the pre-defined features and the respective labels of the documents so that the feature-based model also seeks to classify the new document in accordance with its relevance to pharmacovigilance, wherein the feature-based model utilizes a plurality of decision trees with nodes representing the pre-defined features.

Block 1110 may involve applying an aggregation model to the classifications of the new document produced by the natural language model and the feature-based model, wherein the aggregation model was trained with prior classifications produced by the natural language model and the feature-based model so that the aggregation model seeks to produce a further classification of the new document in accordance with its relevance to pharmacovigilance, wherein the further classification is a weighted combination of classifications produced by the natural language model and the feature-based model for the new document.

In some embodiments, each respective selection within the documents is labelled with a binary value indicating that the selection is either of interest or not of interest to pharmacovigilance.

In some embodiments, the relevance to pharmacovigilance for each of the documents is expressed with a binary value indicating that each of the documents is either of interest or not of interest to pharmacovigilance.

In some embodiments, the relevance to pharmacovigilance for each of the documents is expressed with a probability that each of the documents is of interest to pharmacovigilance.

In some embodiments, the natural language model is a context-free word embedding model.

In some embodiments, the encoders of the natural language model each contain a transformer and a neural network.

In some embodiments, the pre-defined features include terms related to drugs, statistical characteristics, risk scores, designated medical events, adverse medical events, and terms pre-selected to keep under review.

In some embodiments, the pre-defined features also include indications of combinations of the terms appearing a common sentence or consecutive sentences.

In some embodiments, the feature-based model is a gradient-boosting model.

In some embodiments, the aggregation model applies multivariate logistic regression to produce the further classifications.

V. CONCLUSION

The present disclosure is not to be limited in terms of the particular embodiments described in this application, which are intended as illustrations of various aspects. Many modifications and variations can be made without departing from its scope, as will be apparent to those skilled in the art. Functionally equivalent methods and apparatuses within the scope of the disclosure, in addition to those described herein, will be apparent to those skilled in the art from the foregoing descriptions. Such modifications and variations are intended to fall within the scope of the appended claims.

The above detailed description describes various features and operations of the disclosed systems, devices, and methods with reference to the accompanying figures. The example embodiments described herein and in the figures are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations.

With respect to any or all of the message flow diagrams, scenarios, and flow charts in the figures and as discussed herein, each step, block, and/or communication can represent a processing of information and/or a transmission of information in accordance with example embodiments. Alternative embodiments are included within the scope of these example embodiments. In these alternative embodiments, for example, operations described as steps, blocks, transmissions, communications, requests, responses, and/or messages can be executed out of order from that shown or discussed, including substantially concurrently or in reverse order, depending on the functionality involved. Further, more or fewer blocks and/or operations can be used with any of the message flow diagrams, scenarios, and flow charts discussed herein, and these message flow diagrams, scenarios, and flow charts can be combined with one another, in part or in whole.

A step or block that represents a processing of information can correspond to circuitry that can be configured to perform the specific logical functions of a herein-described method or technique. Alternatively or additionally, a step or block that represents a processing of information can correspond to a module, a segment, or a portion of program code (including related data). The program code can include one or more instructions executable by a processor for implementing specific logical operations or actions in the method or technique. The program code and/or related data can be stored on any type of computer readable medium such as a storage device including RAM, a disk drive, a solid-state drive, or another storage medium.

The computer readable medium can also include non-transitory computer readable media such as computer readable media that store data for short periods of time like register memory and processor cache. The computer readable media can further include non-transitory computer readable media that store program code and/or data for longer periods of time. Thus, the computer readable media may include secondary or persistent long-term storage, like ROM, optical or magnetic disks, solid-state drives, compact-disc read only memory (CD-ROM), for example. The computer readable media can also be any other volatile or non-volatile storage systems. A computer readable medium can be considered a computer readable storage medium, for example, or a tangible storage device.

Moreover, a step or block that represents one or more information transmissions can correspond to information transmissions between software and/or hardware modules in the same physical device. However, other information transmissions can be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

While various aspects and embodiments have been disclosed herein, other aspects and embodiments will be apparent to those skilled in the art. The various aspects and embodiments disclosed herein are for purpose of illustration and are not intended to be limiting, with the true scope being indicated by the following claims.

What is claimed is:

1. A computer-implemented method comprising:
   obtaining, from persistent storage, a corpus of documents, wherein each of the documents is labelled with its relevance to pharmacovigilance;
   performing data preparation operations on the documents, wherein the data preparation operations include: de-duplicating the documents, normalizing terminology within the documents, and extracting pre-defined features within the documents, wherein the pre-defined features relate to pharmacovigilance;
   fine-tuning a natural language model with the documents and their labels, wherein the natural language model was pre-trained using scientific or medical literature, and wherein the fine-tuning involves further training of one or more encoders within the natural language model so that the natural language model seeks to classify new documents in accordance with their relevance to pharmacovigilance;

training a feature-based model with the pre-defined features extracted from the documents and the respective labels of the documents so that the feature-based model also seeks to classify the new documents in accordance with their relevance to pharmacovigilance, wherein the feature-based model utilizes a plurality of decision trees with nodes representing the pre-defined features; and training an aggregation model with classifications produced by the natural language model and the feature-based model so that the aggregation model seeks to produce further classifications of the new documents in accordance with their relevance to pharmacovigilance, wherein the further classifications are weighted combinations of classifications produced by the natural language model and the feature-based model for the new documents.

2. The computer-implemented method of claim 1, wherein each respective selection within the documents is labelled with a binary value indicating that the selection is either of interest or not of interest to pharmacovigilance.

3. The computer-implemented method of claim 1, wherein the relevance to pharmacovigilance for each of the documents is expressed with a binary value indicating that each of the documents is either of interest or not of interest to pharmacovigilance.

4. The computer-implemented method of claim 1, wherein the relevance to pharmacovigilance for each of the documents is expressed with a probability that each of the documents is of interest to pharmacovigilance.

5. The computer-implemented method of claim 1, wherein the natural language model is a context-free word embedding model.

6. The computer-implemented method of claim 1, wherein the encoders of the natural language model each contain a transformer and a neural network.

7. The computer-implemented method of claim 1, wherein the pre-defined features include terms related to drugs, statistical characteristics, risk scores, designated medical events, adverse medical events, and terms pre-selected to keep under review.

8. The computer-implemented method of claim 7, wherein the pre-defined features also include indications of combinations of the terms appearing a common sentence or consecutive sentences.

9. The computer-implemented method of claim 1, wherein the aggregation model applies multivariate logistic regression to produce the further classifications.

10. The computer-implemented method of claim 1, further comprising:

storing, in the persistent storage, the natural language model, the feature-based model, and the aggregation model as trained.

11. An article of manufacture including a non-transitory computer-readable medium, having stored thereon program instructions that, upon execution by a computing device, cause the computing device to perform operations comprises:

obtaining, from persistent storage, a corpus of documents, wherein each of the documents is labelled with its relevance to pharmacovigilance;

performing data preparation operations on the documents, wherein the data preparation operations include: de-duplicating the documents, normalizing terminology within the documents, and extracting pre-defined features within the documents, wherein the pre-defined features relate to pharmacovigilance;

fine-tuning a natural language model with the documents and their labels, wherein the natural language model was pre-trained using scientific or medical literature, and wherein the fine-tuning involves further training of one or more encoders within the natural language model so that the natural language model seeks to classify new documents in accordance with their relevance to pharmacovigilance;

training a feature-based model with the pre-defined features extracted from the documents and the respective labels of the documents so that the feature-based model also seeks to classify the new documents in accordance with their relevance to pharmacovigilance, wherein the feature-based model utilizes a plurality of decision trees with nodes representing the pre-defined features; and training an aggregation model with classifications produced by the natural language model and the feature-based model so that the aggregation model seeks to produce further classifications of the new documents in accordance with their relevance to pharmacovigilance, wherein the further classifications are weighted combinations of classifications produced by the natural language model and the feature-based model for the new documents.

12. A computer-implemented method comprising:

obtaining, from persistent storage, a set of pre-defined features and a new document related to a scientific or medical topic, wherein the pre-defined features relate to pharmacovigilance;

normalizing terminology within the new document;

extracting a subset of the pre-defined features from within new document;

applying a natural language model to the new document, wherein the natural language model was pre-trained using scientific or medical literature and fine-tuned using a corpus of documents, wherein each of the documents was labelled with its relevance to pharmacovigilance, and wherein the fine-tuning involved further training of one or more encoders within the natural language model so that the natural language model seeks to classify the new document in accordance with its relevance to pharmacovigilance;

applying a feature-based model to the subset of the pre-defined features extracted from the new document, wherein the feature-based model was trained with the pre-defined features and the respective labels of the documents so that the feature-based model also seeks to classify the new document in accordance with its relevance to pharmacovigilance, wherein the feature-based model utilizes a plurality of decision trees with nodes representing the pre-defined features; and applying an aggregation model to the classifications of the new document produced by the natural language model and the feature-based model, wherein the aggregation model was trained with prior classifications produced by the natural language model and the feature-based model so that the aggregation model seeks to produce a further classification of the new document in accordance with its relevance to pharmacovigilance, wherein the further classification is a weighted combination of classifications produced by the natural language model and the feature-based model for the new document.

13. The computer-implemented method of claim 12, wherein each respective selection within the documents is labelled with a binary value indicating that the selection is either of interest or not of interest to pharmacovigilance.

14. The computer-implemented method of claim 12, wherein the relevance to pharmacovigilance for each of the documents is expressed with a binary value indicating that each of the documents is either of interest or not of interest to pharmacovigilance.

15. The computer-implemented method of claim 12, wherein the relevance to pharmacovigilance for each of the documents is expressed with a probability that each of the documents is of interest to pharmacovigilance.

16. The computer-implemented method of claim 12, wherein the natural language model is a context-free word embedding model.

17. The computer-implemented method of claim 12, wherein the encoders of the natural language model each contain a transformer and a neural network.

18. The computer-implemented method of claim 12, wherein the pre-defined features include terms related to drugs, statistical characteristics, risk scores, designated medical events, adverse medical events, and terms pre-selected to keep under review.

19. The computer-implemented method of claim 18, wherein the pre-defined features also include indications of combinations of the terms appearing a common sentence or consecutive sentences.

20. The computer-implemented method of claim 12, wherein the aggregation model applies multivariate logistic regression to produce the further classifications.

* * * * *